United States Patent [19]

Okazaki

[11] Patent Number: 5,730,903
[45] Date of Patent: Mar. 24, 1998

[54] COMPOUND AND THIN FILM COMPOSED OF THE DISCOTIC COMPOUND

[75] Inventor: Masaki Okazaki, Kanagawa, Japan

[73] Assignee: Fuji Photo Film Co., Ltd., Minami-ashigara, Japan

[21] Appl. No.: 574,683

[22] Filed: Dec. 19, 1995

[30] Foreign Application Priority Data

Dec. 28, 1994 [JP] Japan .................... 6-327027

[51] Int. Cl.$^6$ ............... C09K 19/32; G02F 1/13; C07C 69/76; C07C 61/12
[52] U.S. Cl. ............... 252/299.62; 252/299.01; 349/117; 349/123; 349/183; 349/191; 526/328; 560/117; 562/499
[58] Field of Search ............... 252/299.01, 299.62; 428/1; 349/123, 191, 117, 183; 560/117; 562/499; 526/328

[56] References Cited

U.S. PATENT DOCUMENTS

| | | |
|---|---|---|
| 5,518,783 | 5/1996 | Kawata et al. ............... 428/1 |
| 5,635,105 | 6/1997 | Kawata et al. ............... 252/299.01 |

OTHER PUBLICATIONS

Caplus:1994:192, 333, 1994.
Caplus:1993:70733, 1993.
Shenonda et al. "Synthesis and Properties of Diacetylenic Liquid Crystals," Polymer Preprints, vol. 33, No. 1, Apr. 1992, pp. 1048–1049.
Chien et al, "Synthesis and Properties of Diacetylenic Liquid Crystalline Monomers and Polymers," SPIE vol. 1692 (1992), pp. 159–169.
D. Adam et al, "Fast photoconduction in the highly ordered columnar phase of a discotic liquid crystal", Nature, vol. 371, Sep. 8, 1994.

J. Campbell Scott, "Upwardly mobile organics", Nature, vol. 371, Sep. 8, 1994.

*Primary Examiner*—Shean C. Wu
*Attorney, Agent, or Firm*—Burns, Diane, Swecker & Mathis, LLP

[57] ABSTRACT

A thin film comprising a discotic compound having diacetylene groups at the side chain moiety thereof, and a compound represented by formula (1):

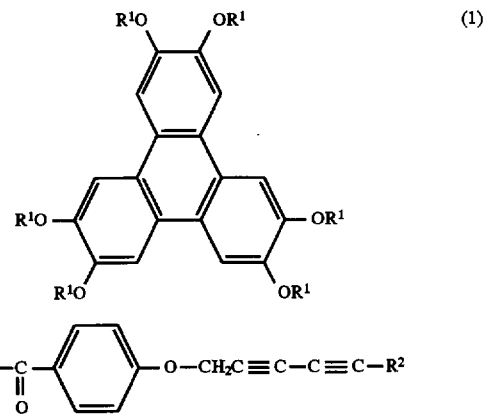

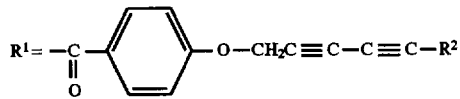

wherein $R^2$ represents an alkyl group or an aryl group.

5 Claims, No Drawings

COMPOUND AND THIN FILM COMPOSED OF THE DISCOTIC COMPOUND

FIELD OF THE INVENTION

The present invention relates to a novel discotic compound useful as an optoelectronic material, a thin film composed thereof, and a polymer thereof.

BACKGROUND OF THE INVENTION

Recently, phthalocyanine derivatives and triphenylene derivatives each having a discotic form are being watched with keen interest as optoelectronic materials and, for example, D. Adam, et al, *Nature*, Vol. 371, page 141 and J. C. Scott, *Nature*, Vol. 371, page 102 report about the positive hole mobility of triphenylene derivatives in liquid crystalline state and mention the possibility of application of these derivatives for various purposes.

A so-called discotic compound having a discotic form can become a liquid crystalline phase called "discotic liquid crystal" by introducing proper side chains. Accordingly, the term "discotic compound" in the present invention means a compound having a core portion of a discotic liquid crystal compound.

Specific examples of a discotic liquid crystal compound are described in C. Destrade, et al., *Mol. Cryst. Liq. Cryst.*, Vol. 71, page 111 (1981); J. Zhand et al, *J. Am. Chem. Soc.*, Vol. 116. page 2655 (1994); and *Kikan Kagaku Sosetsu (Quarterly Chemical Review)*, No. 22, *Ekisho no Kagaku (Chemistry of Liquid Crystal)*, Chapter 5 (pages 50 to 72), Chapter 10, Paragraph 2 (pages 135 to 141), edited by Nippon Kagaku Kai (The Chemical Society of Japan) and these descriptions can be referred to.

In general, the discotic compound has such a structure that the benzene derivative, the triphenylene derivative, the truxene derivative, the phthalocyanine derivative, the porphyrin derivative, the anthracene derivative, the azacrown derivative, the cyclohexane derivative, β-diketone series metal complex derivative or the phenylacetylene macrocycle derivative described in these publications is present as the center mother nucleus (core portion) of the molecule and straight chain alkyl groups or alkoxy groups, substituted benzoyloxy groups, etc., are radially linked to the nucleus as the side chains.

Among these derivatives, the triphenylene derivatives, the truxene derivatives, and the phenylacetylene macrocycle derivatives are liable to comparatively easily form a discotic nematic phase and are attractive compounds. In particular, the triphenylene derivatives are being watched with keen interest.

In *Nature* described above, it is described that a triphenylene derivative has a large positive hole mobility in a specific liquid crystalline phase but since the molecular ordering in the liquid crystalline phase cannot be fixed, there is a description that the development of such a fixation technique is expected. Also, at the same time, it is expected that by inexpensive coating, a thin film wherein the molecular ordering in the liquid crystalline phase is fixed can be produced.

SUMMARY OF THE INVENTION

Accordingly, the first object of the present invention is to provide a compound capable of fixing the molecular ordering in the liquid crystalline phase of a discotic compound and the second object is to provide a compound capable of producing a thin film wherein the molecular ordering in the liquid crystalline phase of a discotic compound is fixed, by coating.

As the result of various investigations, the inventor has found that the objects of the present invention can be attained by using a discotic compound having diacetylene groups at the side chain moiety thereof and also by forming a thin film of the compound and polymerizing the thin film, and has achieved the present invention.

That is, the present invention is as follows.

(1) A thin film comprising a discotic compound having diacetylene groups at the side chain moiety thereof.

(2) The thin film as described in (1) obtained by polymerizing the discotic compound.

(3) The thin film as described in (1), wherein the discotic compound is represented by formula (1) described below.

(4) The thin film as described in (2), wherein the discotic compound is represented by formula (1) described below.

(5) A compound represented by formula (1) described below.

DETAILED DESCRIPTION OF THE INVENTION

The diacetylene group being used in the present invention means a conjugated group and there are groups described, e.g., in L. Braudsma, *Preparative Actyrenic Chemistry*, 2nd ed., published by Elsevier Co., (1988) (Amsterdam) and Masao Kato and Hachiro Nakanishi, *Yuki Hisenkei Kogaku Zairyou (Organic Nonlinear Optical Materials)*, published by CMC K.K., (1985). Among them, the group having such a structure that four methylene chains each composed of continued substituted or unsubstituted alkoxy groups are replaced with conjugated diacetylenes is preferred.

As the discotic compound being used in this invention, there are, for example, the discotic molecular moiety of the mother nucleus of the foregoing discotic liquid crystal compound. The formal feature of the discotic mother nucleus without side chain moiety can be, for example, expressed as follows as to the hydrogen-substituted product which is the original compound.

First, the size of the molecule is determined as follows.

1) About the molecule, the structure as planer as possible, and preferably a planar molecular structure is formed. In this case, as the bonding distance and the bonding angle, it is preferred to use the standard values according the hybridization of the orbit and for example, *Kagaku Binran (Chemical Handbook)*, 4 ed., Basic Edition, the II Separate Volume, Chapter.15, edited by Nippon Kagaku Kai (The Chemical Society of Japan), published by Maruzen K.K. (1993) can be referred to.

2) By using the structure obtained in foregoing 1) as the initial value, the structure is optimized by a molecular orbital theory calculation or a molecular mechanics calculation. As the method, there are, for example, the methods of Gaussian 92, MOPAC 93, CHARMm/QUANTA, and MM3 and the method of Gaussian 92 is preferred.

3) The gravity center of the structure obtained by the structure optimization is moved to the original point and the axes of coordinates are employed as the principal axes of inertia (the principal axes of ellipsoid of inertia).

4) A sphere defined by a van der Waals radius is imparted to each atom, whereby the form of the molecule is described.

5) The length of the direction of each axis of coordinates is measured on the van der Waals surface and they are defined as a, b and c.

By defining the discotic form using a, b, and c obtained by the foregoing procedure, the form can be expressed as a≧b>c and a≧b≧a/2, and preferably a≧b>c and a≧b≧0.7a. Also, it is preferred that b/2>c.

Also, as the practical compounds, there are the derivatives of the mother nucleus compound described, e.g., in *Kikan Kagaku Sosetsu* (*Quarterly Chemical Review*), No. 22, *Ekisho no Kagaku* (*Chemistry of Liquid Crystals*), Chapter 5, Chapter 10, Paragraph 2, edited by Nippon Kagaku Kai (The Chemical Society of Japan), published by Gakkai Shuppan Center, (1994); the C. Destrade et al research report, *Mol. Cryst. Liq. Cryst.*, Vol. 71, page 117 (1981); the B. Kohne et al research report, *Angew. Chem.*, Vol. 96, page 70 (1984), the J. M. Lehn research report, *J. Chem. Soc. Chem. Commun.*, page 1794 (1985); and the J. Zhang, J. S. Moore et al research report, *J. Am. Chem. Soc.*, Vol. 116, page 2655 (1994).

For example, there are benzene derivatives, triphenylene derivatives, truxene derivatives, phthalocyanine derivatives, porphyrin derivatives, anthracene derivatives, azacrown derivatives, cyclohexane derivatives, β-diketone series metal complex derivatives, hexaethynylbenzene derivatives, dibenzopyrene derivatives, coronene derivatives, and the derivatives of phenylacetylene macrocycle. Furthermore, there are compounds such as the cyclic compounds and the hetero-atom substituted isoelectronic structural compounds thereof, etc., described in *Kagaku Sosetsu No. 15, Atarashii Hookozoku Kagaku* (*New Aromatic Chemistry*), edited by Nippon Kagaku Kai (The Chemical Society of Japan), published by Tokyo University, (1977). Also, as the case of the foregoing metal complexes, a discotic molecule formed by the assembly of plural molecules by a hydrogen bond, a coordinate bond, etc., may be used.

As the mother nucleus compound, there are preferably triphenylene and truxene. As the side chain, any material may be used if the material contains the foregoing diacetylene group and the material may contain an alkyl group, an aryl group, or a heterocyclic group. Also, the material may be substituted with the substituents described in C. Hansch, A. Leo, and R. W. Taft, *Chemical Review*, Vol. 91, pages 165–195 (1991), published by American Chemical Society and as typical examples, there are an alkoxy group, an alkyl group, an alkoxycarbonyl group, and a halogen atom. Furthermore, the compound may have a functional group such as, for example, an ether group, an ester group, a carbonyl group, a thioether group, a sulfoxide group, a sulfonyl group, and an amido group in the side chain.

As the compound being used in this invention, the compound represented by formula (A) is preferred and in particular, the compound represented by formula (1) is preferred.

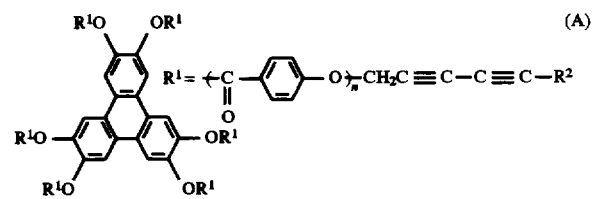
(A)

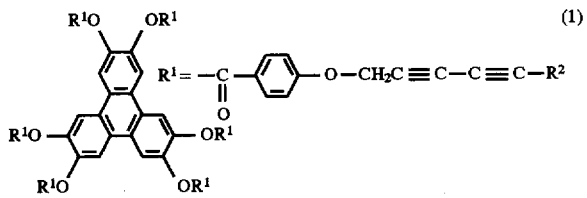
(1)

$R^2$ in the formula (A) or the formula (1) represents an alkyl group or an aryl group. Also, n in the formula (A) represents 0 or 1.

Then, these formulae are explained in detail.

The alkyl group represented by $R^2$ may be unsubstituted or substituted and has from 1 to 20 carbon atoms, preferably from 1 to 15 carbon atoms, and more preferably from 1 to 10 carbon atoms, and examples of the unsubstituted alkyl group are methyl, ethyl, propyl, butyl, pentyl, hexyl, heptyl, octyl, nonyl, decyl, isopropyl, isobutyl, 2-ethylhexyl, and cyclohexyl. Also, as to the substituted alkyl group, as the substituent, there are, for example, a hydroxy group, an acylamino group, an alkoxy group, a vinyl group, a phenyl group, an acyloxy group, an alkylthio group, an alkoxycarbonyl group, an acyl group, and a halogen atom. More practically, there are 2-methoxyethyl, allyl, benzyl, acetoxyethyl, 2-methylthioethyl, 2-chloroethyl, 3-hydroxypropyl, 3-acetyl-aminopropyl, 4-ethoxybutyl, 5-bromopentyl, 6-methoxycarbonylhexyl, and acetylmethyl.

The aryl group represented by $R^2$ may be unsubstituted or substituted and has from 6 to 25 carbon atoms, preferably from 6 to 20 carbon atoms, and more preferably from 6 to 15 carbon atoms. Examples of the unsubstituted aryl group are phenyl and naphthyl and as to the substituted aryl group, as the substituent, there are, for example, an alkyl group, a hydroxy group, an acylamino group, an alkoxy group, a vinyl group, a phenyl group, an acyloxy group, an alkylthio group, an alkoxycarbonyl group, an acyl group, a heterocyclic group, and a halogen atom. More practically, there are, for example, tolyl, 4-propylphenyl, 4-ethoxyphenyl, 4-pentyloxyphenyl, 3-hydroxyphenyl, 4-biphenyl, 3-acetyloxyphenyl, 4-chlorophenyl, 3-methylphenyl, 3,4-methylenedioxyphenyl, 4-ethoxy-3-methylphenyl, 3-fluorophenyl, 4-methoxycarbonylphenyl, 2-fluorophenyl, 4-propionylaminophenyl, 4-acetylphenyl, 4-(2-methoxyethoxy)phenyl, and 4-tetrahydrofurfuryloxyphenyl.

In these groups, unsubstituted alkyl groups are preferred and in particular, the straight chain unsubstituted alkyl groups are preferred.

Then, specific examples of the compound of the present invention are shown below. However, the scope of the present invention is not limited to these compounds only. Specific examples of $R^2$ and n in the formula (A) are shown.

| Comp. | n | R² |
|---|---|---|
| 1 | 0 | CH₃ |
| 2 | 1 | CH₃ |
| 3 | 0 | C₂H₅ |
| 4 | 1 | C₂H₅ |
| 5 | 0 | n-C₃H₇ |
| 6 | 1 | n-C₃H₇ |
| 7 | 0 | n-C₄H₉ |
| 8 | 1 | n-C₄H₉ |
| 9 | 0 | n-C₅H₁₁ |
| 10 | 1 | n-C₅H₁₁ |
| 11 | 0 | n-C₆H₁₃ |
| 12 | 1 | n-C₆H₁₃ |
| 13 | 0 | n-C₇H₁₅ |
| 14 | 1 | n-C₇H₁₅ |
| 15 | 0 | n-C₈H₁₇ |
| 16 | 1 | n-C₈H₁₇ |
| 17 | 0 | n-C₉H₁₉ |
| 18 | 1 | n-C₉H₁₉ |
| 19 | 0 | n-C₁₀H₂₁ |
| 20 | 1 | n-C₁₀H₂₁ |
| 21 | 0 | CH₂CH=CH₂ |
| 22 | 1 | CH₂CH=CH₂ |
| 23 | 0 | C₆H₅ |
| 24 | 1 | C₆H₅ |
| 25 | 0 | CH₂C₆H₅ |
| 26 | 1 | CH₂C₆H₅ |
| 27 | 0 | p-C₆H₄—CH₃ |
| 28 | 1 | p-C₆H₄—CH₃ |
| 29 | 0 | i-C₃H₇ |
| 30 | 1 | i-C₃H₇ |
| 31 | 0 | —CH₂—C₃H₅(cyclo) |
| 32 | 1 | —CH₂—C₃H₅(cyclo) |
| 33 | 0 | cyclohexyl |
| 34 | 1 | cyclohexyl |
| 35 | 0 | —CH₂CH₂OCH₃ |
| 36 | 1 | —CH₂CH₂OCH₃ |
| 37 | 0 | —CH₂OCOCH₃ |
| 38 | 1 | —CH₂OCOCH₃ |
| 39 | 0 | —CH₂OSO₂C₆H₅ |
| 40 | 1 | —CH₂OSO₂C₆H₅ |
| 41 | 0 | —CH₂OCOC₂H₅ |
| 42 | 1 | —CH₂OCOC₂H₅ |
| 43 | 0 | —CH₂CH₂OCOCH₃ |
| 44 | 1 | —CH₂CH₂OCOCH₃ |
| 45 | 0 | —CH₂CH₂SCH₃ |
| 46 | 1 | —CH₂CH₂SCH₃ |
| 47 | 0 | -2-ethylhexyl |
| 48 | 1 | -2-ethylhexyl |

-continued

| Comp. | n | R² |
|---|---|---|
| 49. | (triphenylene with 6 OR¹ groups) | R¹=—C(=O)—(pyridine)—OCH₂C≡C—C≡C—C₂H₅ |
| 50. | (triphenylene with 6 OR¹ groups) | R¹=—C(=O)—(furan)—CH₂OCH₂C≡C—C≡C—C₃H₇ |
| 51. | (triphenylene with 6 OR¹ groups) | R¹=—(CH₂)₅—C≡C—C≡C—CH₃ |

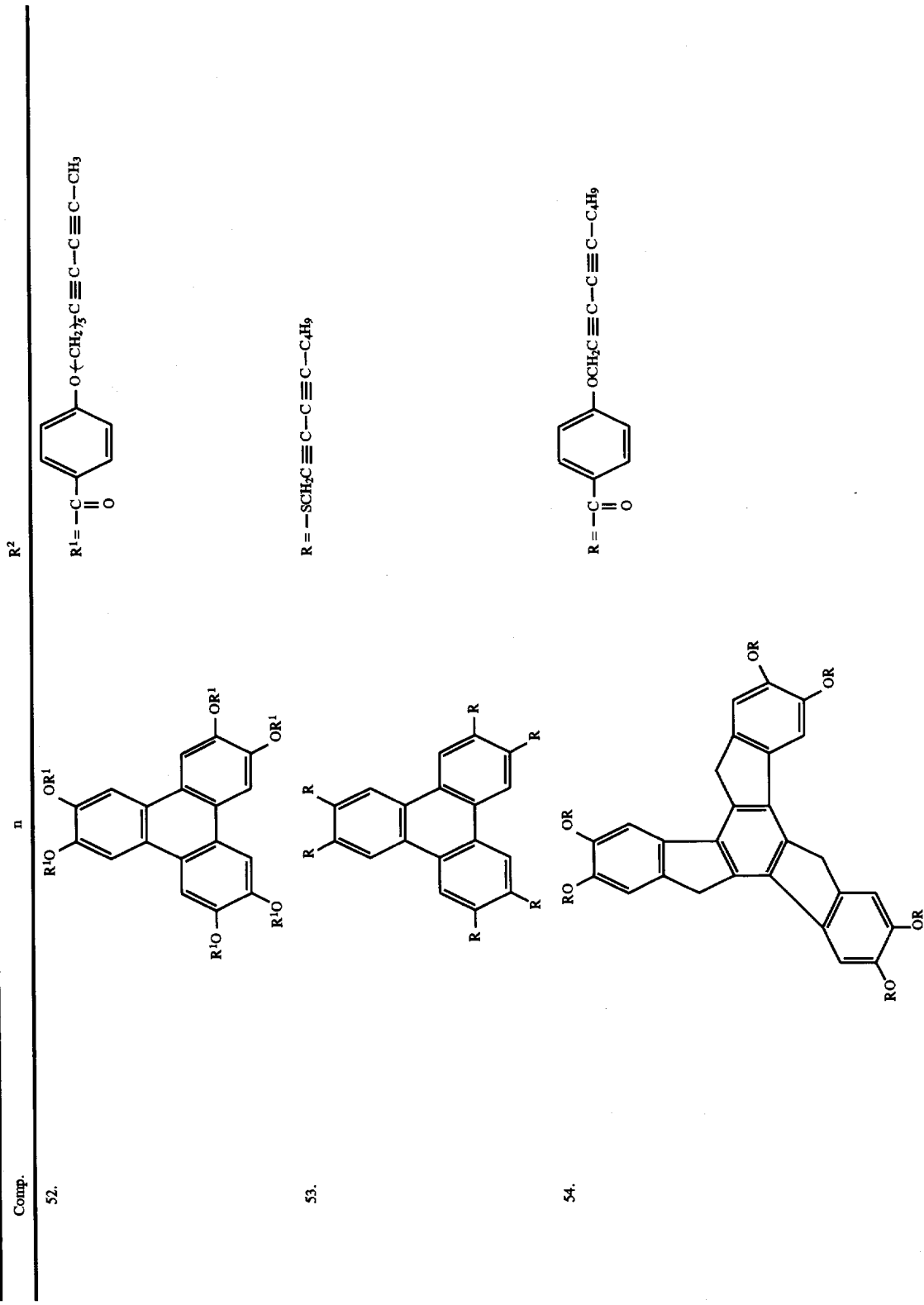

-continued

| Comp. | n | R² |
|---|---|---|
| 55. | | R = —CH₂C≡C—C≡C—C₄H₉ |
| 56. | | R = —SCH₂C≡C—C≡C—C₅H₁₁ |

| Comp. | n | R² |
|---|---|---|
| 57. | | 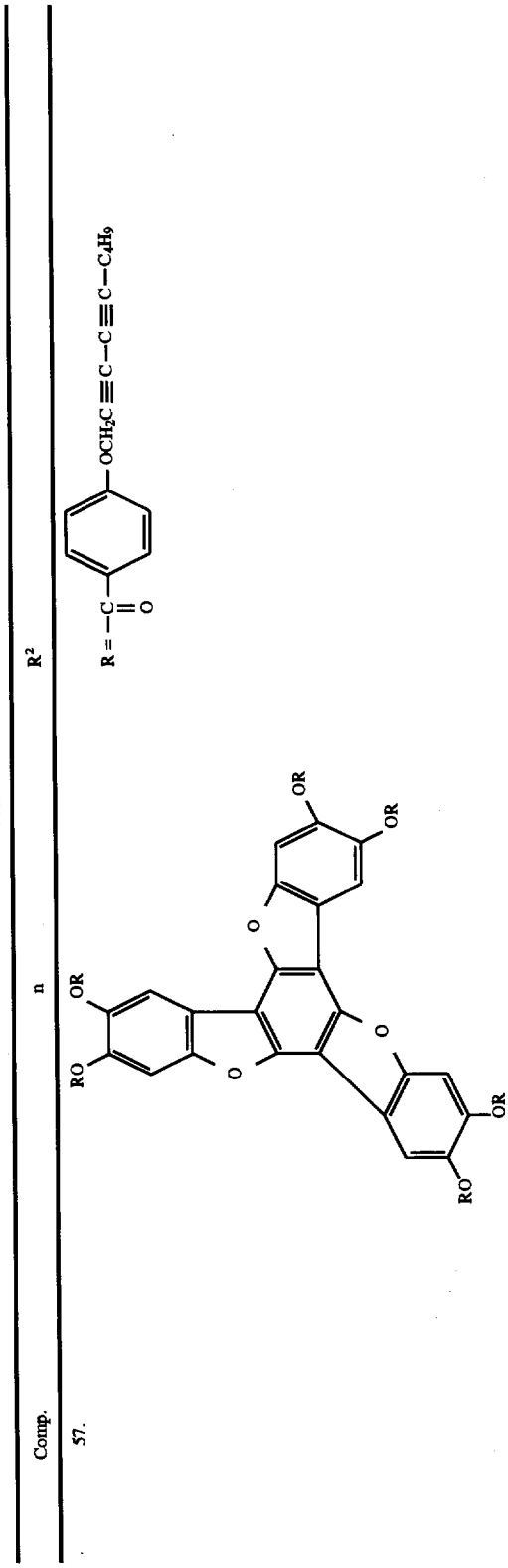 R = —OCH₂C≡C—C≡C—C₄H₉ |
| 58. | | 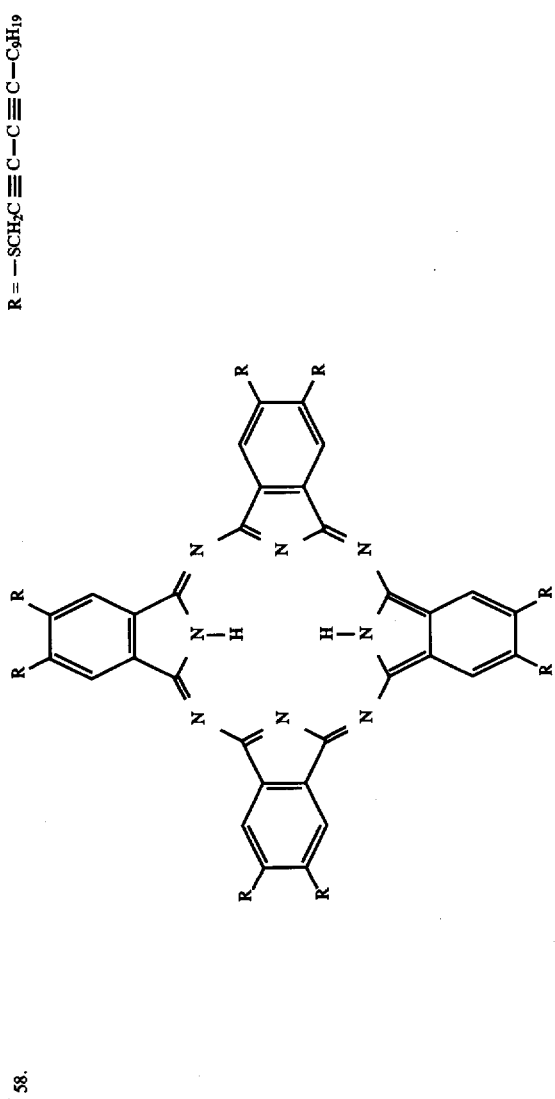 R = —SCH₂C≡C—C≡C—C₉H₁₉ |

-continued

| Comp. | n | R² |
|---|---|---|
| 59. | [Cu phthalocyanine structure with R substituents] | R = —SCH₂C≡C—C≡C—C₇H₁₅ |
| 60. | [cyclam-type macrocycle with four N—R groups] | R = —C(=O)—C₆H₄—OCH₂C≡C—C≡C—C₅H₁₁ |
| 61. | [sugar (inositol/glucose) with six OR groups] | R = —OCH₂C≡C—C≡C—C₅H₁₁ |

-continued

| Comp. | n | R² |
|---|---|---|
| 62. | Cu complex with four 3,4-(OR)₂-phenyl groups coordinated via O–Cu–O | R = −C(=O)−C₆H₄−OCH₂C≡C−C≡C−C₄H₉ |
| 63. | Hexa-OR triphenylene | R = −C(=O)−C₆H₄−O(CH₂)₄C≡C−C≡C−C₄H₉ |
| 64. | Hexa-OR triphenylene | R = −C(=O)−C₆H₄−O(CH₂CH₂O)₂CH₂C≡C−C≡C−CH₃ |

-continued

| Comp. | n | R² |
|---|---|---|
| 65. | [triphenylene with 6 OR groups] | R = —(CH₂CH₂O)₂CH₂C≡C—C≡C—CH₃ |
| 66. | [triphenylene with 6 OR groups] | R = [4-substituted phenyl]—C(=O)—O(CH₂CH₂O)₂CH₂C≡C—C≡C—CH₂C₆H₅ |
| 67. | [triphenylene with 6 OR groups] | R = —(CH₂CH₂O)₂CH₂C≡C—C≡C—CH₂C₆H₅ |

The compound represented by the formula (A) can be synthesized by the etherification reaction (n=0) or the esterification reaction (n=1) of the side chain moiety and 2,3,6,7,10,11-hexahydroxytriphenylene. The synthesis of the side chain moiety, in particular, the diacetylene moiety can be carried out by referring to the L. Graudsma's literature described above.

The etherification reaction and the esterification reaction can be carried out by referring to the methods described in S. R. Sandler and W. Karo, "Organic Functional Group Preparations", Vol. 1 and Vol. 2 (Academic Press Co, New York, London, 1968).

The solvent being used for these reactions can be selected from polar solvents such as N,N-dimethylformamide (DMF), dimethyl sulfoxide (DMSO), etc., and non-polar solvents such as benzene, hexene, etc. Also, the polar solvents such as DMF, N,N-dimethylacetamide, etc.; pyridine; ethers such as tetrahydrofuran, 1,2-dimethoxyethane, etc.; and halogenated solvents such as dichloromethane, chloroform, etc., are preferably used and a mixed solvent can be also used. In these solvents, amides, ketones, and ethers are preferable.

For these reactions, if necessary, a catalyst can be used. As a basic catalyst, an organic catalyst or an inorganic catalyst may be used and for example, there are sodium hydroxide, potassium hydroxide, sodium methoxide, sodium ethoxide, potassium-t-butoxide, pyridine, triethylamine, piperidine, 1,8-diazabicyclo[5,4,0]-7-undecene (DBU), sodium carbonate, potassium carbonate, sodium hydrogencarbonate, sodium acetate, and potassium acetate. In these catalysts, carbonates and amines are preferred and in the case of amines, they may be also used as a solvent.

The reaction temperature can be selected in the range of from $-80°$ C. to $150°$ C., preferably from $-20°$ C. to $100°$ C., and more preferably from $-5°$ C. to $60°$ C.

The discotic liquid crystal composition being used in this invention may be constituted not only by a discotic compound having a single diacetylene group or plural diacetylene groups at the side chain moiety but also by containing the discotic compound having a single diacetylene group or plural diacetylene groups at the side chain moiety and the discotic compounds described in Japanese Patent Application Nos. 6-97443 an 7-41276 and further the compounds described in Japanese Patent Application Nos. 7-110511, 7-221186, and 7-222785. Also, the thin film constituted by using the composition may be constituted by the discotic liquid crystal composition only and in general, at least one layer of the thin film is formed on a support and according to the uses, a protective film or a support may exist on both surfaces of the liquid crystal layer or between the liquid crystal layers. The thickness of the thin film of the present invention is preferably not thicker than 20 μm, and the thin films may be laminated.

The material for the support has preferably a good light transmittance as well as is preferably near an optical isotropic. Accordingly, a support formed by a material having a small intrinsic birefringence value, such as a glass and those commercially available as the trade names of Zeonex (made by Nippon Zeon Co., Ltd.), ARTON (Japan Synthetic Rubber Co., Ltd.), Fujitac (made by Fuji Photo Film Co., Ltd.), etc., is preferred. However, even a material having a large intrinsic birefringence value, such as polycarbonate, polyacrylate, polysulfone, polyether sulfone, etc., can form an optically isotropic support by controlling the molecular orientation at film forming and they can be suitably utilized.

As the material for the protective film, there are, for example, polymeric materials such as polymethyl methacrylate, an acrylic acid-methacrylic acid copolymer, a styrene-anhydrous maleimide copolymer, polyvinyl alcohol, N-methylolacrylamide, a styrene-vinyltoluene copolymer, chlorosulfonated polyethylene, nitrocellulose, polyvinyl chloride, chlorinated polyolefin, polyester, polyimide, a vinyl acetate-vinyl chloride copolymer, an ethylene-vinyl acetate copolymer, polyethylene, polypropylene, polycarbonate, etc.; and organic materials such as a silane coupling agent, etc. Also, a built-up film formed from ω-tricosanoic acid, dioctadecyldimethyl-ammonium chloride, methyl stearate, etc., by a Langmuir-Blodgett method (LB method) can be used.

Also, it is a well-known fact in the case of a rod-form liquid crystal that a protective film previously formed on a support frequently gives a large influence on the molecular orientation at the formation of the liquid crystal layer as an orientation film and the protective film is almost always used as an inorganic or organic orientation film. This is one of the techniques being preferably used in the present invention and as a metal obliquely vapor-deposited film, a SiO obliquely vapor-deposited film is a typical one and as an organic orientation film, a rubbed polyimide film is a typical one, but as other orientation films, a rubbed denatured poval, a rubbed glass substrate treated with a silylating agent, rubbed gelatin film, etc., are used. However, in place of rubbing, a method of stretching a thin film of polyvinyl alcohol to from 4 to 5 times, a method of directly rubbing a glass substrate without specifically forming the foregoing protective film thereon, etc., can be used.

As other method of orienting the discotic liquid crystal formed on a substrate by coating, there are a magnetic orientation and an electric orientation. In the method, after forming the discotic liquid crystal on a substrate by coating, a zone of applying a magnetic field or an electric field at a desired angle is necessary and in this case, it is necessary that the zone itself is adjusted to a temperature at which the liquid crystalline phase is formed.

The liquid crystal layer constituting the thin film of the present invention can be formed as a thin film on a support by a vapor deposition method or a coating method such as spin coating, dip coating, extrusion coating, etc. In particular, in the liquid crystal being used in this invention, a tendency that the optical axes are uniformly directed to the coating direction at the step of coating is frequently observed.

Accordingly, a desired thin film of the present invention can be obtained by forming the liquid crystal thin film on a proper support in a state that at least one interface is in contact with a vapor phase, that is, by a general coating method, after drying, heat-treating the dried film at a temperature within the liquid crystal forming temperature range, for a definite time while forming a discotic nematic phase or a uniaxial columnar phase, and then thermally polymerizing the film as it is or after photocrosslinking polymerizing the film, cooling it.

As coating the compound, it is preferred to use the compound as the solution thereof and as a solvent being used, a solvent having a boiling point of from $30°$ C. to $200°$ C., preferably from $60°$ C. to $150°$ C., and more preferably from $70°$ C. to $130°$ C. under the atmospheric pressure is used. For example, there are 2-butanone, 2,4-dimethyl-3-pentanone, ethyl acetate, 1-butanol, fluorobenzene, and 1,2-dimethoxyethane.

As the photopolymerization initiator being used in the present invention, there are the α-carbonyl compounds described in U.S. Pat. Nos. 2,367,661 and 2,367,670; the acyloin ethers described in U.S. Pat. No. 2,448,828; the aromatic acyloin compounds each substituted with an α-hydrocarbon described in U.S. Pat. No. 2,722,512; the polynuclear quinone compounds described in U.S. Pat. Nos. 3,046,127 and 2,951,758; the combination of triarylimidazole dimer and p-aminophenyl ketone described in U.S. Pat. No. 3,549,367; the acridine compounds and the phenadine compounds described in JP-A-60-105667 (the term "JP-A" as used herein means an "unexamined published Japanese patent application") and U.S. Pat. No. 4,239,850; and the oxadiazole compounds described in U.S. Pat. No. 4,212,970. The concentration of the photopolymerization initiator system in the composition being used in the present invention may be usually slight and if the concentration is unsuitable high, undesirable results such as the interception of effective light, etc., occur. The amount of the photopolymerization initiator system in this invention is sufficiently in the range of from 0.01% to 20% of the coating composition excluding the solvent and more preferably, when the amount is from 0.5% to 5%, good results are obtained.

Furthermore, in the present invention, if necessary, various organic amine compounds can be used together, whereby the effects of the present invention (that is, the easiness of polymerization in the case of photopolymerization) can be increased. Examples of these organic amine compounds are triethanolamine, diethanolaniline, p-dimethylaminobenzoic acid ethyl ester, and Michler's ketone. The addition amount of the organic amine compound is preferably from 50 to 200% of the total amount of the photopolymerization initiators.

Moreover, if necessary, by adding a hydrogen donative compound such as N-phenylglycine, 2-mercaptobenzothiazole, an N,N-dialkylaminobenzoic acid alkyl ester, etc., to the photopolymerization initiator being used in this invention, the photopolymerization initiating faculty can be more increased.

Also, for restraining the hindrance of the polymerization with oxygen, addition of a small amount of a surface active agent is frequently effective.

Furthermore, as a light for the polymerization, electron beams, ultraviolet rays, visible light, or infrared rays (heat rays) can be, if necessary, used but, in general, ultraviolet rays are used. As the light source thereof there are a low-pressure mercury lamp (a sterilization lamp, a fluorescent chemical lamp, a black light), a high-pressure discharging lamp (a high-pressure mercury lamp, a metal halide lamp), and a short arc discharging lamp (a super high-pressure mercury lamp, a xenon lamp, a mercury xenon lamp).

In the case of the benzoyloxytriphenylene ring compound of the present invention, since the compound has generally the $\lambda_{max}$ at about 270 nm and the molecular extinction coefficient thereof is large, it sometimes happens that ultraviolet rays of a short wavelength of 254 nm, etc., are not effectively used.

Accordingly, as the photopolymerization initiator, the compounds described below each having an absorption in the near ultraviolet region and a light source capable of strongly emitting near ultraviolet rays, such as a high-pressure mercury lamp, a metal halide lamp, etc., is preferably used.

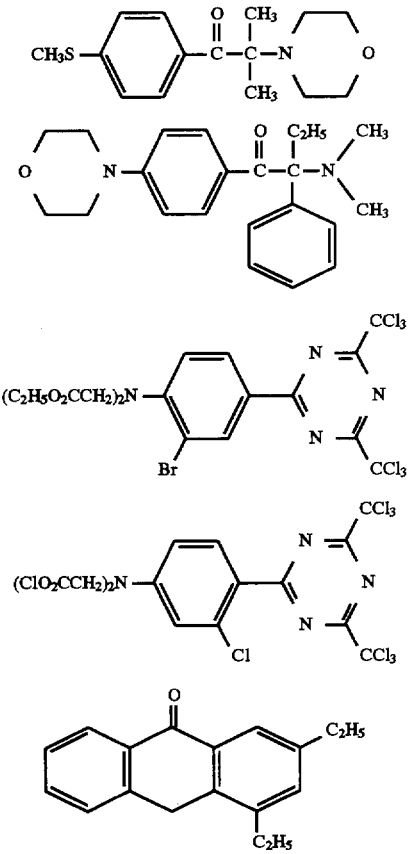

Then, the present invention is explained in more detail based on the following examples.

EXAMPLE 1

Synthesis of Compound 8

1. Synthesis of 4-(2,4-nonadiynyloxy)benzoic acid:

According to the method described in T. Ando et al, *Bull. Chem. Soc. Japan*, Vol. 45, pages 2611–1615 (1972), 3-bromo-2-propyn-1-ol was synthesized. Then, using the product, according to the method described in *Bull. Soc. Chim. France*, pages 1468–1472 (1971), 2,4-nonadiyn-1-ol was synthesized and further 1-chloro-2,4-nonadiyne was synthesized.

In a flask were placed 3.78 g (0.024 mole) of 1-chloro-2,4-nonadiyne thus obtained, 3.32 g (0.02 mole) of ethyl 4-hydroxybenzoate, 5.5 g (0.04 mole) of potassium carbonate, and 50 ml of acetone and the mixture was refluxed by heating for 11 hours. After allowing to cool the reaction mixture to room temperature, the reaction mixture was poured in 250 ml of ice-water and the product was extracted with methylene chloride. After distilling off the solvent of the organic layer, the residue formed was purified by a silica gel column chromatography(developing solvent: hexane/ethyl acetate=3/1) to provide 4.0 g (yield 70%) of ethyl 4-(2,4-nonadiynyloxy)-benzoate.

$^1$H-nmr (δ in CDCl$_3$): 0.9(t, 3H), 1.3–1.6(m, 7H), 2.3(t, 2H), 4.4(q, 2H), 4.8(S, 2H), 7.0(d, 2H), 8.0(d, 2H)

In a flask were placed 4.0 g (0.014 mole) of the benzoate derivative obtained and 18 ml of ethanol and while stirring the mixture at room temperature, an aqueous solution composed of 2.0 g (0.36 mole) of potassium hydroxide and 20 ml of water was added to the mixture. After stirring the mixture for 24 hours at 40° C. Twenty (20) ml of water was added to the mixture followed by ice-cooled. When the reaction mixture was acidified with concentrated hydrochloric acid, white crystals formed. The crystals were recovered by filtration, washed with water, and dried. Thus, 3.2 g (yield 89.3%) of the desired product could be obtained. The melting point was 165°–166° C.

$^1$H-nmr ($\delta$ in CDCl$_3$): 0.9(t, 3H), 1.5(m, 4H), 2.3(t, 2H), 4.8(S, 2H), 7.0(d, 2H), 8.1(d, 2H)

2. Synthesis of Compound 8:

In a flask were placed 1.43 g (12.5 mmoles) of methanesulfonyl chloride and 10 ml of THF and the mixture was stirred under ice-cooling. To the mixture was added dropwise a solution composed of 3.2 g (12.5 mmoles) of the benzoic acid derivative obtained in the above step, 1.61 g (12.5 mmoles) of diisopropylethylamine, and 10 ml of THF at a temperature of not higher than 8° C. After stirring the mixture for 20 minutes under ice-cooling, a suspension composed of 1.61 g (12.5 mmoles) of diisopropylethylamine, 0.15 g (1.25 mmole) of 4-(N,N-dimethylamino)pyridine, 0.41 g (1.25 mmole) of 2,3,6,7,10,11-hexahydroxytriphenylene, and 5 ml of THF was added to the mixture. After stirring the resultant mixture for 2 hours at room temperature, the mixture was allowed to stand overnight. Then, the reaction mixture was poured in 125 ml of ice-water, the product was extracted with methylene chloride, and after distilling off the solvent from the organic layer, the residue was purified by a silica gel column chromatography (development solvent: methylene chloride). Thus, 1.8 g (yield 81%) of the desired product was obtained, wherein a liquid crystalline phase was observed in the range of from 150° C. to 168° C.

$^1$H-nmr ($\delta$ in CDCl$_3$): 0.9(t, 18H), 1.4(q, 12H), 1.5 (q, 12H), 2.3(t, 12H), 4.7(S, 12H), 6.7(d, 12H), 7.85(d, 12H), 8.3(S, 6H)

EXAMPLE 2

Synthesis of Compound 16

1. Synthesis of 4-(2,4-tridecadiynyloxy)benzoic Acid:

The desired compound could be synthesized by the same method as for the synthesis of 4-(2,4-nonadiynyloxy) benzoic acid described in Example 1. $^1$H-nmr of the compound obtained after the recrystallization with acetonitrile is shown below.

$^1$H-nmr ($\delta$ in CDCl$_3$): 0.9(t, 3H), 1.15 to 1.45(m, 10H), 1.55(qi, 2H), 2.30(t, 2H), 4.83(s, 2H), 7.05(d, 2H), 8.10(d, 2H)

2. Synthesis of Compound 16:

The compound could be synthesized by the same method as for the synthesis of Compound 8 described in Example 1. When the phase transition of the compound obtained was observed by a polarization microscope, texture which was considered to be a liquid crystalline phase was observed at a temperature of from room temperature to 121° C. and the transition to an isotropic phase was observed at a temperature from 121° C. to 129° C.

In DSC, an exothermic phenomenon was seen at a temperature of from 66° C. to 76° C. and an endothermic phenomenon was seen at a temperature of from 113° C. to 128° C. (the peak was 123° C.).

$^1$H-nmr ($\delta$ in CDCl$_3$): 0.90(t, 18H), 1.15 to 1.48(m, 60H), 1.55(qi, 12H), 2.30(t, 12H), 4.71(s, 12H), 6.70(d, 12H), 7.88(d, 12H), 8.30(s, 6H)

EXAMPLE 3

Synthesis of Compound 24

1. Synthesis of 4-(5-phenyl-2,4-pentadiynyloxy) benzoic Acid:

The compound could be synthesized by the same method as for the synthesis of 4-(2,4-nonadiynyloxy)benzoic acid described in Example 1. $^1$H-nmr of the compound obtained after the recrystallization with acetone is shown below.

$^1$H-nmr ($\delta$ in DMSO-d$_6$): 5.15(s, 2H), 7.13(d, 2H), 7.45 (m, 3H), 7.60(d, 2H), 7.95(d,

2. Synthesis of Compound 24:

The compound could be synthesized by the same method as for the synthesis of Compound 8 described in Example 1. When the phase transition of the compound obtained was observed by a polarization microscope, the transition to a liquid crystal was observed at 181° C. Thereafter, when the temperature was raised to 300° C., the compound was not transferred to an isotropic phase and was colored and fixed.

$^1$H-nmr ($\delta$ in CDCl$_3$): 4.80 (s, 12H), 6.65 (d, 12H), 7.34(m, 18H), 7.50(d, 12H), 7.89(d, 12H), 8.30(s, 6H)

EXAMPLE 4

Thin Film Preparation—1:

A 2-butanone solution of 20% by weight Compound 8 was spin-coated on a glass plate. Then, while heating the glass plate to 156° C., ultraviolet rays of 254 nm were irradiated. The time of heating and irradiating was 30 minutes. After cooling the coated film to 40° C., when the film was observed by a polarization microscope, the existence of an optical anisotropy could be confirmed. Also, the thin film formed was firm. After heating the glass plate to 200° C. for 5 minutes, when the film was observed by the polarization microscope at that temperature, the optical anisotropy was maintained. This is considered that the molecular ordering was fixed by polymerization.

EXAMPLE 5

Thin Film Preparation—2:

A 2-butanone solution of 20% by weight Compound 8 was spin-coated on a glass plate having been coated with a denatured poval MP-203 (made by Kuraray Co., Ltd.) and rubbed. Then, as the results of carrying out the same procedure as in Example 2 except that the glass plate was heated to 153° C., the optical anisotropy was also maintained in this case. This is considered that the molecular ordering is fixed by polymerization.

EXAMPLE 6

Thin Film Preparation—3

A 2-butanone solution of 20% by weight a mixture of Compound 8 and Compound A of 1/1 by weight ratio was prepared and 0.5% by weight Irgacure 907 (trade name, made by Ciba-Geigy Aktiengesellschaft) was added to the solution. Then, the same procedure as in Example 4 was carried out using the solution thus obtained at the same temperature. In this case, the optical anisotropy was also maintained. This is considered that the molecular arrangement was fixed by polymerization.

Compound A

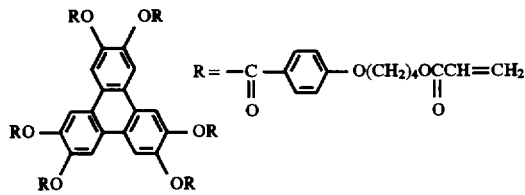

In addition, in the case of the triphenylene derivative used in the above example of this invention, when the compound is collated with the discotic formal feature described above, in the case of a=1, b and c are 0.89 and 0.29, respectively.

By using the compound of the present invention, a thin film of a discotic compound can be formed and the molecular ordering in the liquid crystalline phase can be fixed.

While the invention has been described in detail and with reference to specific embodiments thereof, it will be apparent to one skilled in the art that various changes and modifications can be made therein without departing from the spirit and scope thereof.

What is claimed is:

1. A thin film comprising a discotic compound having diacetylene groups at the side chain moiety thereof, said discotic compound being a liquid crystalline compound and said discotic compound being a triphenylene derivative.

2. The thin film as claimed in claim 1 obtained by polymerizing the discotic compound.

3. A thin film comprising a discotic compound having diacetylene groups at the side chain moiety thereof, said discotic compound being a liquid crystalline compound, wherein the discotic compound is represented by formula (1):

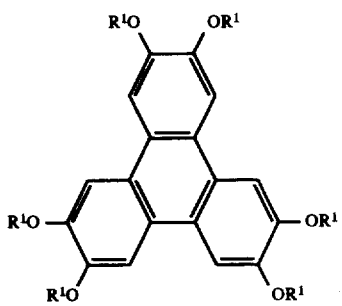

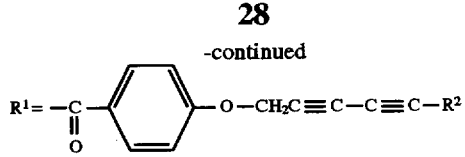

wherein $R^2$ represents an alkyl group having from 1 to 20 carbon atoms or an aryl group having from 6 to 25 carbon atoms.

4. The thin film as claimed in claim 2, wherein the discotic compound is represented by formula (1):

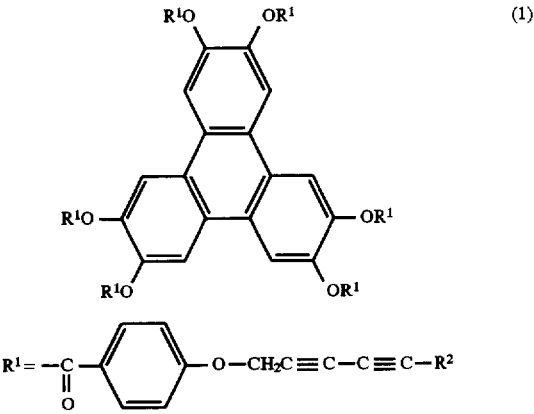

wherein $R^2$ represents an alkyl group having from 1 to 20 carbon atoms or an aryl group having from 6 to 25 carbon atoms.

5. A compound represented by formula (1):

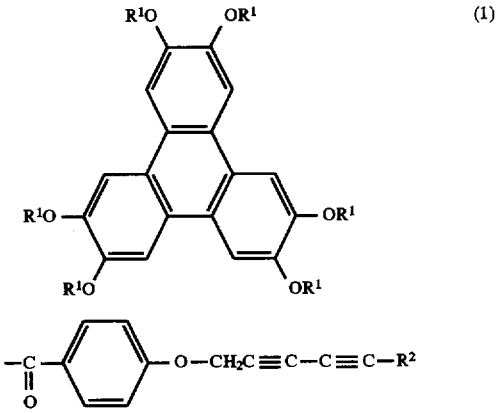

wherein $R^2$ represents an alkyl group having from 1 to 20 carbon atoms or an aryl group having from 6 to 25 carbon atoms.

* * * * *